(12) United States Patent
Chang et al.

(10) Patent No.: US 9,970,882 B2
(45) Date of Patent: May 15, 2018

(54) LIGHT-EMITTING STRUCTURE

(71) Applicants: Fu Tai Hua Industry (Shenzhen) Co., Ltd., Shenzhen (CN); HON HAI PRECISION INDUSTRY CO., LTD., New Taipei (TW)

(72) Inventors: Chih-Kuang Chang, New Taipei (TW); Li Jiang, Shenzhen (CN); Dong-Hai Li, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 472 days.

(21) Appl. No.: 14/594,347

(22) Filed: Jan. 12, 2015

(65) Prior Publication Data

US 2016/0109377 A1 Apr. 21, 2016

(30) Foreign Application Priority Data

Oct. 15, 2014 (CN) .......................... 2014 1 0543684

(51) Int. Cl.
*G01N 21/88* (2006.01)

(52) U.S. Cl.
CPC ... *G01N 21/8806* (2013.01); *G01N 2201/062* (2013.01)

(58) Field of Classification Search
CPC .. F21V 19/0015; F21V 29/74; F21V 33/0052; F21V 19/02; F21V 19/042; F21V 19/045; F21V 23/006; F21V 5/048; F21V 23/004; F21V 23/005; F21V 29/004; F21W 2131/40; F21W 2131/20; F21Y 2103/33; F21Y 2105/10; F21Y 2115/10; G01N 15/0205; G01N 2021/8835; G01N 21/00; G01N 21/17; G01N 21/8803; G01N 21/8851; G01N 21/8806; G01N 21/8845; G01N 2201/062; G01N 21/9036; H05K 2201/10106; F21K 9/20; G02B 5/32
See application file for complete search history.

(56) References Cited

U.S. PATENT DOCUMENTS

| | | | | |
|---|---|---|---|---|
| 5,179,474 A | * | 1/1993 | Bailey | G02B 27/024 250/224 |
| 5,920,643 A | * | 7/1999 | White | G01N 21/8806 362/249.04 |
| 5,943,125 A | * | 8/1999 | King | G01N 21/8806 250/559.34 |
| 6,554,452 B1 | * | 4/2003 | Bourn | G01N 21/8806 313/113 |
| 7,824,077 B2 | * | 11/2010 | Chen | F21V 23/009 362/294 |
| 8,605,284 B2 | * | 12/2013 | Toriumi | G01N 21/474 356/445 |

(Continued)

*Primary Examiner* — Hargobind S Sawhney
(74) *Attorney, Agent, or Firm* — ScienBiziP, P.C.

(57) ABSTRACT

A light-emitting structure includes a base, a light-emitting assembly arranged on the base, a cover configured to be covered over the light-emitting assembly, and a coupling member configured to couple the cover to the base. The light-emitting assembly emits light onto a workpiece to be inspected by an image inspection device. The light-emitting assembly is circular, and a lens of the image inspection device is rotationally coupled to the base.

15 Claims, 5 Drawing Sheets

(56) References Cited

U.S. PATENT DOCUMENTS

| | | | | |
|---|---|---|---|---|
| 8,872,114 B2* | 10/2014 | Nakanishi | ......... | G01N 21/3586 |
| | | | | 250/338.1 |
| 2003/0067774 A1* | 4/2003 | Lizotte | ................... | G02B 5/32 |
| | | | | 362/236 |
| 2007/0206183 A1* | 9/2007 | Lebens | ................. | G01N 21/21 |
| | | | | 356/237.2 |
| 2008/0024794 A1* | 1/2008 | Miyazaki | .......... | G01N 21/8806 |
| | | | | 356/612 |
| 2010/0259750 A1* | 10/2010 | Oka | .................. | G01N 21/9501 |
| | | | | 356/237.3 |
| 2011/0285988 A1* | 11/2011 | Menachem | ........ | G01N 21/8806 |
| | | | | 356/237.5 |
| 2012/0206927 A1* | 8/2012 | Miyahara | ............. | F21V 29/004 |
| | | | | 362/382 |

* cited by examiner

LIGHT-EMITTING STRUCTURE

FIELD

The subject matter herein generally relates to light-emitting structures, and more particularly to a light-emitting structure for emitting light of different colors onto a workpiece to be inspected.

BACKGROUND

Generally, a workpiece can be inspected by an inspection device. Surfaces of the workpiece may be illuminated for inspection.

BRIEF DESCRIPTION OF THE DRAWINGS

Implementations of the present technology will now be described, by way of example only, with reference to the attached figures.

DETAILED DESCRIPTION

Figure 1:
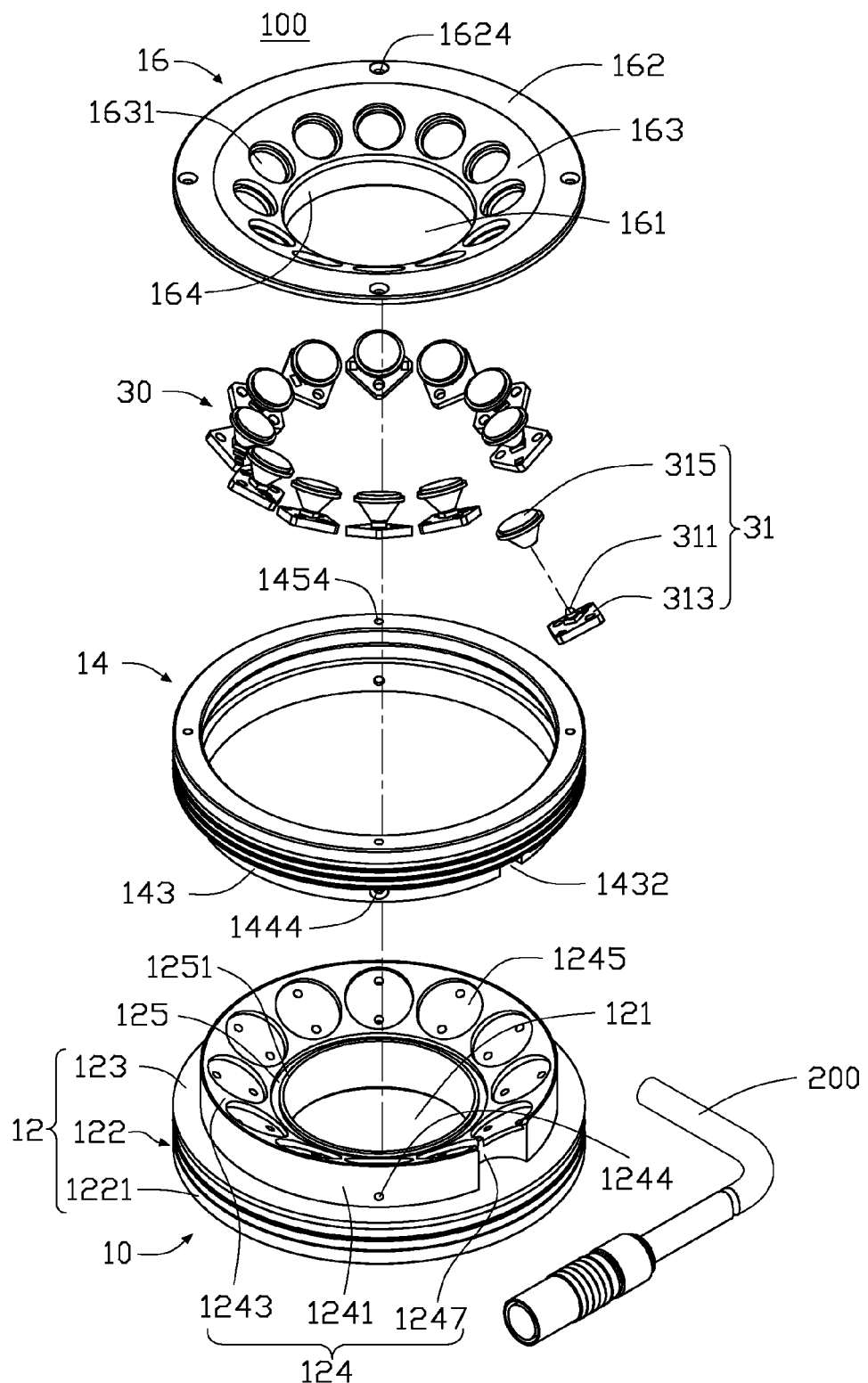
FIG. 1 is an exploded, isometric view of an embodiment of a light-emitting structure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other word that "substantially" modifies, such that the component need not be exact. For example, "substantially cylindrical" means that the object resembles a cylinder, but can have one or more deviations from a true cylinder. The term "comprising" means "including, but not necessarily limited to"; it specifically indicates open-ended inclusion or membership in a so-described combination, group, series and the like.

FIG. 1 illustrates an embodiment of a light-emitting structure 100. The light-emitting structure 100 can include a base 10, a coupling member 14, a cover 16, and a light-emitting assembly 30. The light-emitting assembly 30 can comprise a plurality of light-emitting elements 31 arranged on the base 10. The coupling member 14 can couple the cover 16 to the base 10. In at least one embodiment, the light-emitting structure 100 can be coupled to an image detecting device (not shown) to detect images taken of a workpiece (not shown). The light-emitting assembly 30 can emit light onto the workpiece to illuminate surfaces of the workpiece, and the image detecting device can detect images of the workpiece. The image detecting device can include a lens (not shown) to capture the images of the workpiece.

The base 10, the coupling member 14, and the cover 16 can be substantially circular. A first through hole 121 can be defined in the base 10. A second through hole 141 can be defined in the coupling member 14. A third through hole 161 can be defined in the cover 16. The base 10, the coupling member 14, and the cover 16 can share a common axis, and the common axis passes through the first through hole 121, the second through hole 141, and the third through hole 161. The lens of the image detecting device can be rotationally coupled to the light-emitting structure 100 and received in the first through hole 121.

The base 10 can include a supporting portion 12 and a holding portion 124. The holding portion 124 can protrude from a supporting surface 123 of the supporting portion 12. In the illustrated embodiment, the holding portion 124 and the supporting portion 12 are both substantially circular and coaxial with each other, and the first through hole 121 passes through the supporting portion 12 and the holding portion 124. A diameter of the supporting portion 12 is larger than a diameter of the holding portion 124.

The holding portion 124 can include a holding wall 1241 protruding from the supporting surface 123, and a holding surface 1243 coupled between the holding wall 1241 and the supporting surface 123. Thus, the holding surface 1243 is slanted relative to the holding wall 1241 and the supporting surface 123. In the illustrated embodiment, the holding surface 1243 is slanted toward the common axis. The holding surface 1243 can define a plurality of holding grooves 1245 for holding the plurality of light-emitting elements 31. In at least one embodiment, a number of the holding grooves 1245 equals a number of the light-emitting elements 31, and each light-emitting element 31 is received in one corresponding holding groove 1245. The holding grooves 1245 can be spaced apart and arranged around the first through hole 121. Thus, the light-emitting elements 31 emit light toward the common axis.

The supporting portion 12 can form a flange rim 1251 surrounding the first through hole 121. A coupling groove 125 can be defined between the flange rim 1251 and the holding surface 1243. The coupling groove 125 can surround the flange rim 1251. A plurality of heat-dissipating strips 1221 can protrude from a periphery 122 of the supporting portion 12. The heat-dissipating strips 1221 can be spaced from each other and dissipate heat generated by the light-emitting assembly 30.

A first cutout 1247 can be defined through the holding wall 1241 and the holding surface 1243. A first portion of a connecting line 200 can be received in the first cutout 1247 to provide power to the light-emitting elements 31, and a second portion of the connecting line 200 can be coupled to a controller (not shown). The controller can control the light-emitting assembly 30 to operate.

The coupling member 14 can be supported on the supporting surface 123 of the base 10 and surround the holding portion 124. In the illustrated embodiment, the coupling member 14 is substantially circular, and the holding portion 124 is received in the second through hole 141. A second cutout 1432 can be defined in a sidewall 143 of the coupling member 14. The second cutout 1432 can align with the first cutout 1247 to allow the first portion of the connecting line 200 to pass through to be received in the first cutout 1247. A plurality of first securing holes 1244 can be defined in the holding wall 1241 of the base 10, and a plurality of second securing holes 1444 can be defined in the sidewall 143 of the coupling member 14. A plurality of securing members (not shown) can be received through the first securing holes 1244 and the second securing holes 1444 to secure the coupling member 14 to the base 10.

Figure 2:
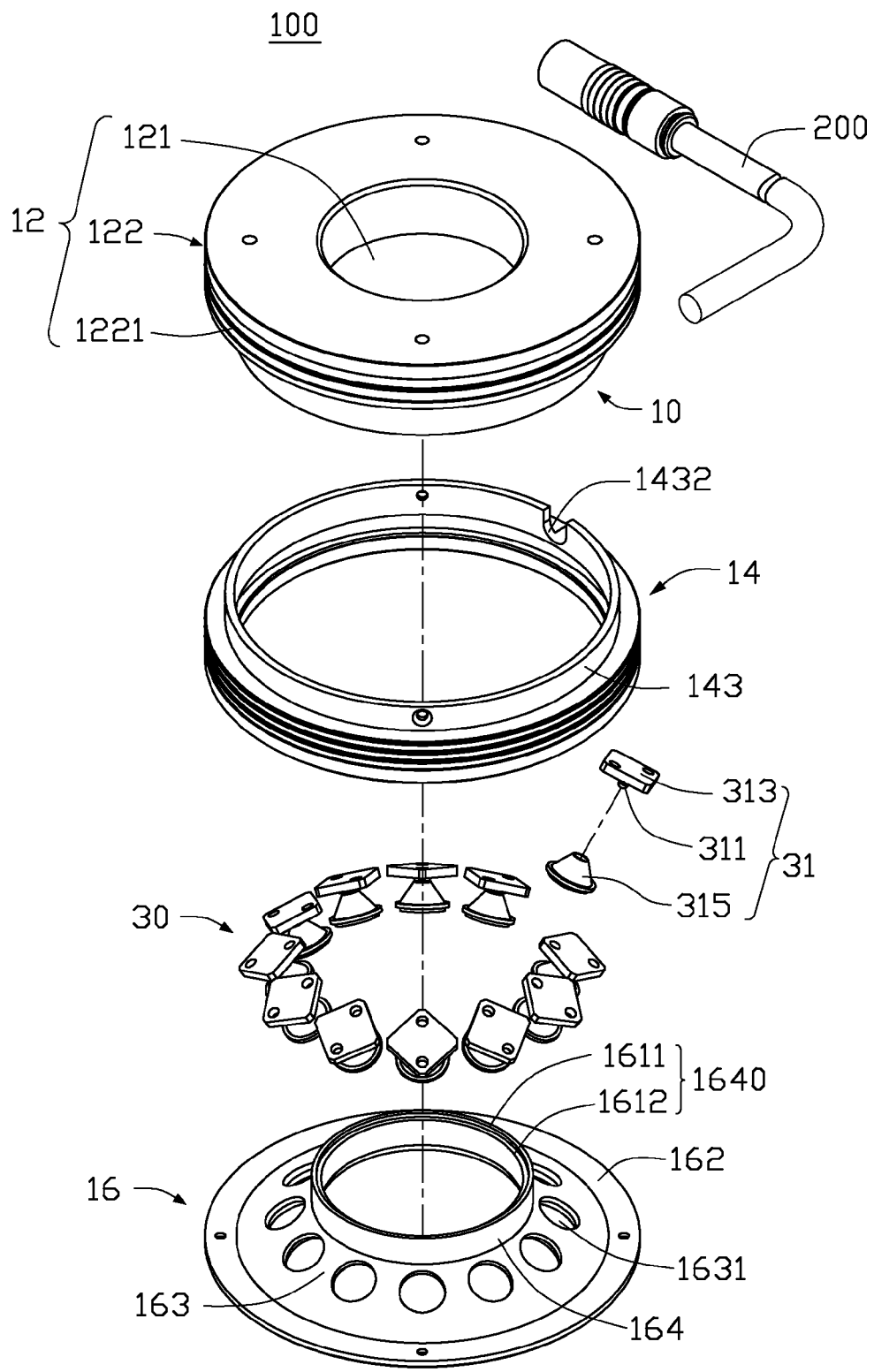
FIG. 2 is similar to FIG. 1, but viewed from a different angle.
Figure 3:
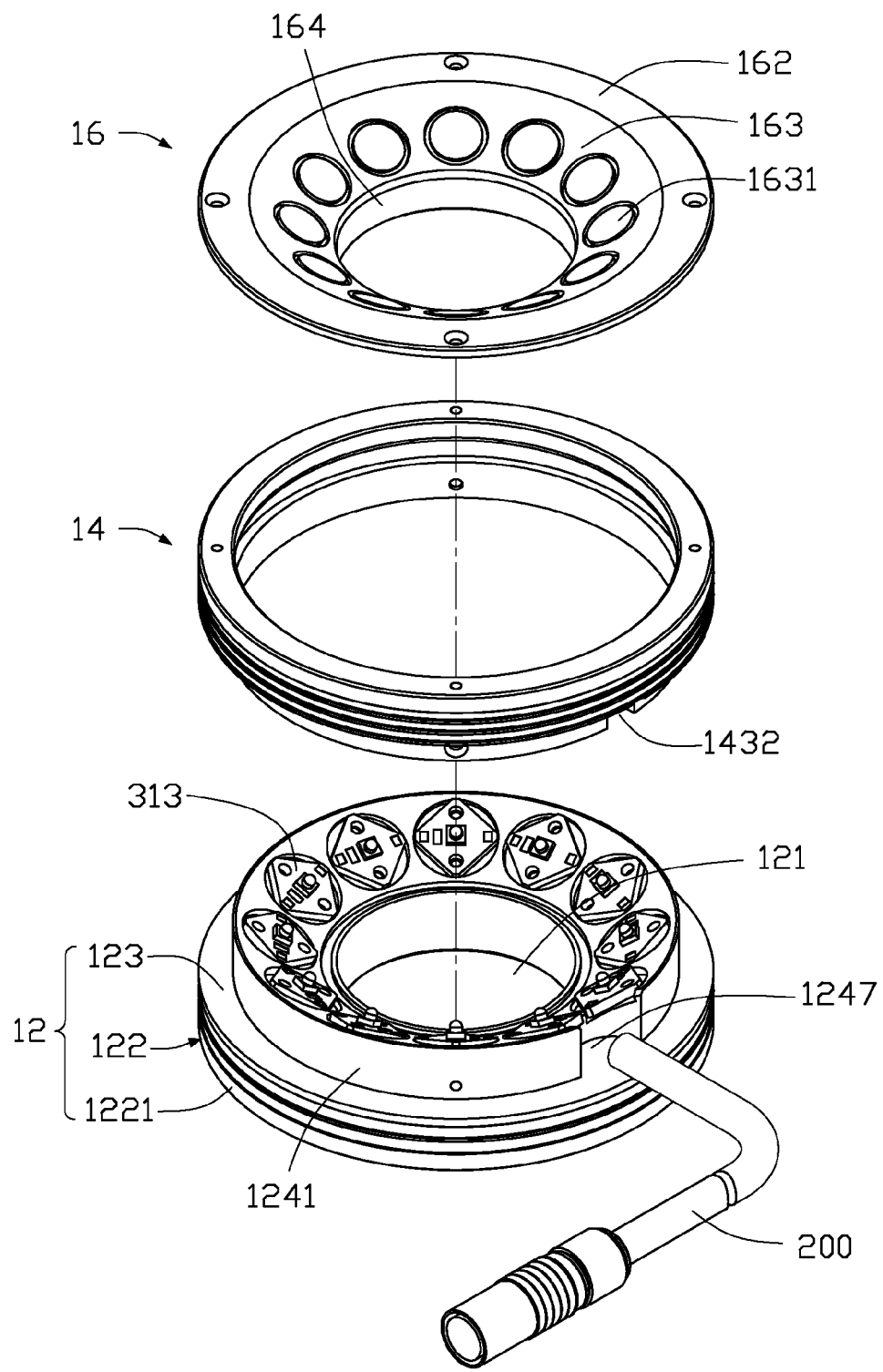
FIG. 3 is a partially assembled, isometric view of the light-emitting structure of FIG. 1.
Figure 4:
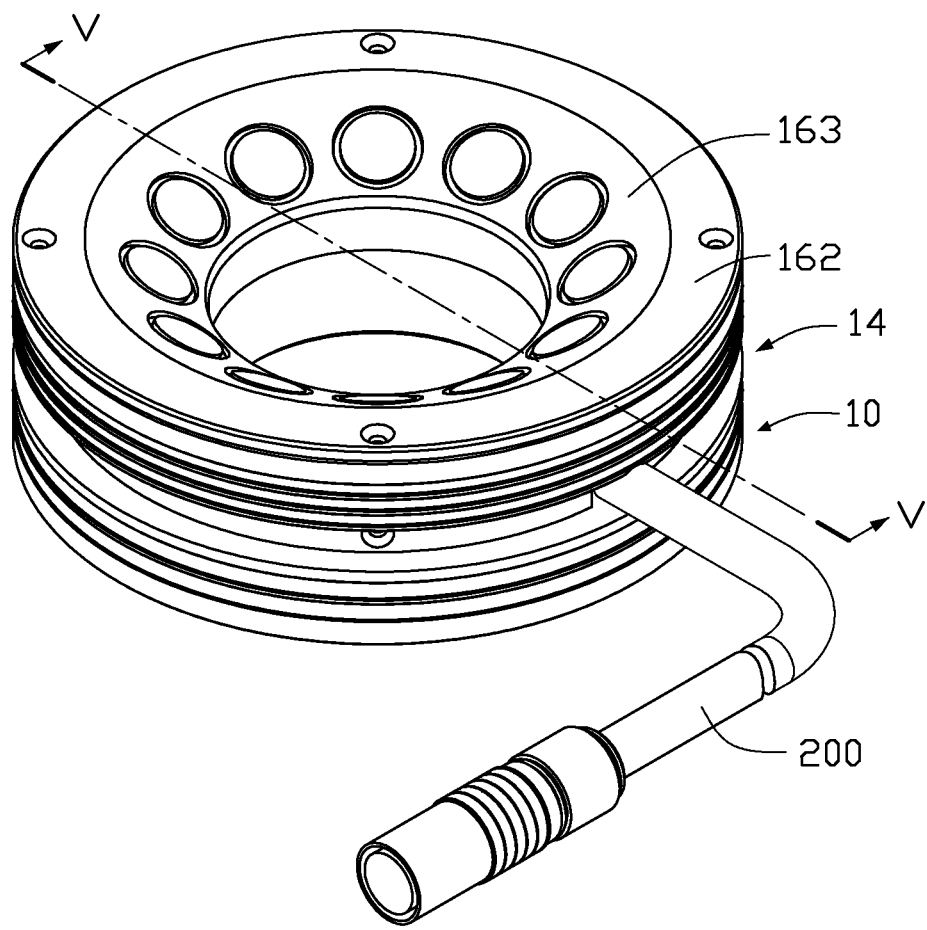
FIG. 4 is an assembled, isometric view of the light-emitting structure of FIG. 1.
Figure 5:
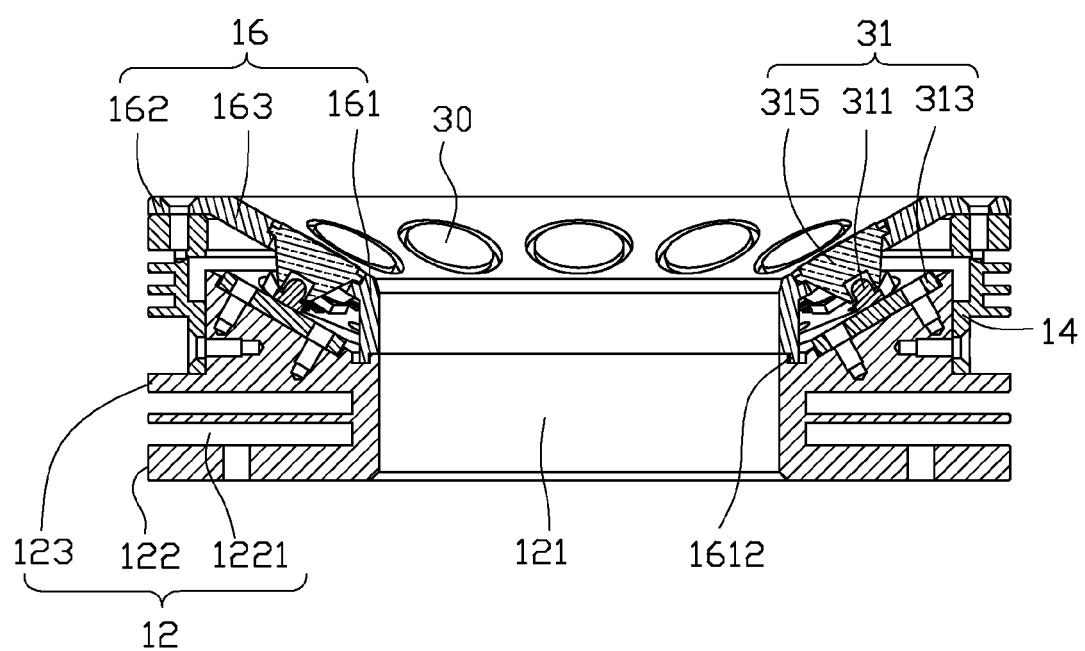
FIG. 5 is a cross-sectional view taken along line V-V of FIG. 4.

Referring to FIGS. 1 and 2, the cover 16 can include a coupling rim 162, a covering surface 163, and a coupling flange 164. In the illustrated embodiment, the coupling rim 162, the covering surface 163, and the coupling flange 164 are substantially circular, and the third through hole 161 passes through the coupling rim 162, the covering surface 163, and the coupling flange 164. The covering surface 163 can be coupled between the coupling rim 162 and the coupling flange 164, and be slanted relative to the coupling rim 162 and the coupling flange 164. A plurality of third securing holes 1624 can be defined in the coupling rim 162, and a plurality of fourth securing holes 1454 can be defined in the coupling member 14. The cover 16 can be secured to the coupling member 14 by a plurality of securing members (not shown) being received through the third securing holes 1624 and the fourth securing holes 1454. A plurality of emitting holes 1631 can be defined in the covering surface 163. In at least one embodiment, a number of the emitting holes 1631 is equal to the number of holding grooves 1245. When the light-emitting structure 100 is assembled, the covering surface 163 can cover over the holding surface 1243, and each emitting hole 1631 is aligned with one corresponding holding groove 1245.

A distal end of the coupling flange 164 can form a stepped surface 1640. The stepped surface 1640 can include a first stepped portion 1611 and a second stepped portion 1612. When the light-emitting structure 100 is assembled, the first stepped portion 1611 can be received in the coupling groove 125 of the base 10, and the second stepped portion 1612 can be supported on the flange rim 1251.

In at least one embodiment, a number of the light-emitting elements 31 is equal to the number of the holding grooves 1245 and the number of emitting holes 1631. Each light-emitting element 31 can include a printed circuit board 313, a light emitter 311, and a light cover 315. In at least one embodiment, the light emitter is a light-emitting diode (LED) of a designated color. The light-emitting assembly 30 can be composed of a plurality of groups of light-emitting elements (not labeled). In the illustrated embodiment, there are twelve light-emitting elements 31, and the twelve light-emitting elements 31 are divided into four groups, each group including three light-emitting elements 31. Each light-emitting element 31 of each group of light-emitting elements emits light of a different color. In at least one embodiment, each group of light-emitting elements can emit red, blue, and green light. The light-emitting elements 31 can be arranged in sequence of alternating colors around the first through hole 121. When the light-emitting structure 100 is assembled, the first portion of the connecting line 200 can provide power to each of the printed circuit boards 313 of the light-emitting elements 31 through the corresponding holding grooves 1245. The light covers 315 can be transparent, and a material of the light covers 315 is resistant to damage by a maximum temperature of the light emitters 311.

Referring to FIGS. 1-5, when the light-emitting structure 100 is assembled, the printed circuit boards 313 of the light-emitting elements 31 are received in the corresponding holding grooves 1245 of the base 10, and the light covers 315 of the light-emitting elements 31 are received in the corresponding emitting holes 1631 of the cover 16. The light-emitting assembly 30 can emit light of different colors onto the workpiece according to a color of the workpiece, and the lens of the image detection device can be rotationally coupled to the light-emitting structure 100.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A light-emitting structure comprising:
   a base comprising a supporting portion and a holding portion, the holding portion protruding from a supporting surface of the supporting portion; the supporting portion and the holding portion being circular; the supporting portion and the holding portion being coaxial with each other; a diameter of the supporting portion being larger than a diameter of the holding portion; the base defining a first through hole; the first through hole passing through the supporting portion and the holding portion;
   a light-emitting assembly arranged on the base and configured to emit light;
   a cover configured to cover over the light-emitting assembly; and
   a coupling member configured to couple the cover to the base;
   wherein the cover, and the coupling member are circular;
   a second through hole is defined through the coupling member;
   a third through hole is defined through the cover;
   the base, the coupling member, and the cover share a common axis, and the common axis passes through the first through hole, the second through hole, and the third through hole;
   the light-emitting assembly comprises a plurality of light-emitting elements;
   wherein the holding portion comprises a holding wall protruding from the supporting surface of the supporting portion, and a holding surface coupled between the holding wall and the supporting surface of the supporting portion;
   the holding surface is slanted relative to the holding wall and the supporting surface and the holding surface defines a plurality of holding grooves;
   the holding grooves are spaced apart and arranged around the first through hole;
   each light-emitting element is received in one corresponding holding groove; and the light-emitting elements emit light toward the common axis.

2. The light-emitting structure as in claim 1, wherein:
   the supporting portion forms a flange rim surrounding the first through hole; and a coupling groove is defined between the flange rim and the holding surface of the holding portion and surrounds the flange rim.

3. The light-emitting structure as in claim 1, wherein:
the supporting portion of the base comprises a plurality of heat-dissipating strips protruding from a periphery of the supporting portion;
the plurality of heat-dissipating strips are spaced apart; and
the plurality of heat-dissipating strips are configured to dissipate heat generated by the light-emitting assembly.

4. The light-emitting structure as in claim 1, wherein:
a first cutout is defined through the holding wall and the holding surface;
a first portion of a connecting line is received in the first cutout to provide power to the plurality of light-emitting elements; and
a second portion of the connecting line is coupled to a controller, the controller being configured to control the light-emitting assembly to operate.

5. The light-emitting structure as in claim 4, wherein:
the coupling member is supported on the supporting surface of the supporting portion and surrounds the holding portion of the base;
a second cutout is defined in a sidewall of the coupling member; and
the second cutout is aligned with the first cutout, when the coupling member is coupled to the base.

6. The light-emitting structure as in claim 1, wherein:
the coupling member is supported on the supporting surface of the supporting portion and surrounds the holding portion of the base;
the holding portion is received in the second through hole of the coupling member;
a plurality of first securing holes is defined in the holding wall of the holding portion of the base;
a plurality of second securing holes is defined in a sidewall of the coupling member; and
the coupling member is secured to the base by a plurality of securing members received through the plurality of first securing holes and the plurality of second securing holes.

7. The light-emitting structure as in claim 1, wherein:
the cover comprises a coupling rim, a covering surface, and a coupling flange;
the coupling rim, the covering surface, and the coupling flange are circular;
the third through hole passes through the coupling rim, the covering surface, and the coupling flange;
the covering surface is coupled between the coupling rim and the coupling flange;
the coupling rim is configured to be coupled to the coupling member;
the covering surface is slanted relative to the coupling rim and is covered over the holding surface of the holding portion of the base; and
the coupling flange is coupled to the supporting portion of the base.

8. The light-emitting structure as in claim 7, wherein:
a plurality of emitting holes is defined in the covering surface of the cover;
a number of the emitting holes is equal to a number of the holding grooves defined in the holding surface of the holding portion of the base;
each of the plurality of emitting holes is aligned with one corresponding holding groove;
a diameter of the coupling rim is larger than a diameter of the coupling flange;
a distal end of the coupling flange forms a stepped surface comprising a first stepped portion and a second stepped portion;
the first stepped portion of the coupling flange is received in the coupling groove of the supporting portion of the base; and
the second stepped portion of the coupling flange is supported on the flange rim of the supporting portion of the base.

9. The light-emitting assembly as in claim 8, wherein:
each of the plurality of light-emitting elements comprises a printed circuit board, at least one light emitter coupled to the printed circuit board, and a light cover;
the light cover is covered over the light emitter;
the printed circuit board of each of the plurality of light-emitting elements is received in one corresponding holding groove of the holding portion of the base;
the light cover is received in one corresponding emitting hole of the cover;
the at least one light emitter emits light through the light cover; and
the first portion of the connecting line provides power to each of the printed circuit boards of the light-emitting elements through the corresponding holding grooves.

10. The light-emitting structure as in claim 9, wherein the at least one light-emitter of each of the plurality of light-emitting elements is an LED of a designated color.

11. The light-emitting structure as in claim 9, wherein each of the plurality of light-emitting elements comprises a plurality of light emitters of different colors.

12. The light-emitting structure as in claim 9, wherein:
each light cover is transparent, and a material of each light cover is resistant to damage by a maximum temperature of the light emitter;
the light-emitting assembly is composed of a plurality of groups of light-emitting elements, and each light-emitting element of each group of light-emitting elements emits light of a different color; and
the light-emitting elements of the groups of light-emitting elements are arranged in sequence of alternating colors around the first through hole.

13. The light-emitting structure as in claim 7, wherein:
a plurality of third securing holes is defined in the coupling rim;
a plurality of fourth securing holes is defined in the coupling member; and
the cover is secured to the coupling member by a plurality of securing members passing through the plurality of third securing holes and the plurality of fourth securing holes.

14. The light-emitting structure as in claim 7, wherein:
an inner diameter of the coupling flange of the base is the same as a diameter of the first through hole; and
an inner diameter of the coupling rim of the cover is larger than an inner diameter of the coupling flange of the cover.

15. The light-emitting structure as in claim 1, wherein a diameter of a boundary between the holding surface and the supporting surface is smaller than a diameter of a boundary between the holding surface and the holding wall.

* * * * *